(12) United States Patent
Yoshihara (10) Patent No.: US 10,761,027 B2
(45) Date of Patent: Sep. 1, 2020

(54) IMAGE PROCESSING APPARATUS AND COMPUTER-READABLE RECORDING MEDIUM STORING PROGRAM

(71) Applicant: Konica Minolta, Inc., Chiyoda-ku, Tokyo (JP)

(72) Inventor: Yuka Yoshihara, Hino (JP)

(73) Assignee: Konica Minolta, Inc., Chiyoda-ku, Tokyo (JP)

( * ) Notice: Subject to any disclaimer, the term of this patent is extended or adjusted under 35 U.S.C. 154(b) by 176 days.

(21) Appl. No.: 16/069,640

(22) PCT Filed: Jan. 13, 2017

(86) PCT No.: PCT/JP2017/000965
§ 371 (c)(1),
(2) Date: Jul. 12, 2018

(87) PCT Pub. No.: WO2017/126420
PCT Pub. Date: Jul. 27, 2017

(65) Prior Publication Data
US 2018/0372642 A1  Dec. 27, 2018

(30) Foreign Application Priority Data
Jan. 19, 2016 (JP) .................................. 2016-007778

(51) Int. Cl.
G06K 9/00 (2006.01)
G01N 21/64 (2006.01)
(Continued)

(52) U.S. Cl.
CPC ..... *G01N 21/6458* (2013.01); *G01N 21/6428* (2013.01); *G01N 33/48* (2013.01);
(Continued)

(58) Field of Classification Search
CPC ........... G01N 21/6458; G01N 21/6428; G01N 21/6456; G01N 21/64; G01N 21/645;
(Continued)

(56) References Cited

U.S. PATENT DOCUMENTS

2003/0231791 A1* 12/2003 Torre-Bueno ...... G01N 21/6428
382/133
2005/0037406 A1* 2/2005 De La Torre-Bueno ....................
G01N 21/6428
435/6.12
(Continued)

FOREIGN PATENT DOCUMENTS

EP  2833123  2/2015
JP  2011-179924  9/2011
(Continued)

OTHER PUBLICATIONS

Notice of Reasons for Refusal issued in JP Application No. 2017-562541 dated Sep. 30, 2019.
(Continued)

*Primary Examiner* — Jose L Couso
(74) *Attorney, Agent, or Firm* — BakerHostetler (57) ABSTRACT

An image processing apparatus includes: an input receiver into which a fluorescent image and a morphological image are input; and a controller. The fluorescent image represents expression of a plurality of kinds of biological substances in a tissue specimen in which a fluorescent bright spot represents expression of the biological substances. The morphological image represents morphology of a cell in the tissue specimen and includes a range common to the fluorescent image. The controller extracts an observation target region from the morphological image, extracts the fluorescent bright spot from the fluorescent image, and calculates a statistical value from a number of the plurality of kinds of
(Continued)

biological substances whose expression is represented by the fluorescent bright spots.

13 Claims, 4 Drawing Sheets

(51) Int. Cl.
| | | |
|---|---|---|
| *G06T 7/00* | (2017.01) | |
| *G01N 33/48* | (2006.01) | |
| *G06T 7/136* | (2017.01) | |
| *G06T 7/155* | (2017.01) | |
| *G06K 9/62* | (2006.01) | |
| *G06T 7/11* | (2017.01) | |
| *G01N 33/533* | (2006.01) | |
| *G01N 1/30* | (2006.01) | |

(52) U.S. Cl.
CPC ....... *G01N 33/533* (2013.01); *G06K 9/00147* (2013.01); *G06K 9/6215* (2013.01); *G06T 7/0012* (2013.01); *G06T 7/11* (2017.01); *G06T 7/136* (2017.01); *G06T 7/155* (2017.01); *G01N 1/30* (2013.01); *G01N 2021/6439* (2013.01); *G06T 2207/10056* (2013.01); *G06T 2207/10064* (2013.01); *G06T 2207/30024* (2013.01)

(58) Field of Classification Search
CPC ........... G01N 21/6452; G01N 21/6445; G01N 21/6486; G01N 1/30; G01N 2021/6439; G01N 2021/6421; G01N 2021/6419; G01N 33/48; G01N 33/533; G01N 33/582; G01N 33/53; G01N 33/543; G01N 33/54313; G01N 2015/1488; G01N 2015/1443; G01N 15/1475; G01N 15/1434; G01N 15/1459; G01N 15/1463; G06T 2207/10056; G06T 2207/10064; G06T 2207/30024; G06T 2207/20021; G06T 2207/20104; G06T 2207/20221; G06T 2207/30096; G06T 2207/20036; G06T 7/136; G06T 7/155; G06T 7/11; G06T 7/0012; G06T 7/90; G06T 1/00; G06T 1/0007; G06K 9/6215; G06K 9/00147; G06K 9/0014; G06K 9/4661; G02B 21/0004; G02B 21/086; G02B 21/26; G02B 21/367; G02B 21/16; G02B 21/365; G02B 26/008; H04N 7/183; G06F 19/321; G16H 15/00; A61B 5/0071
See application file for complete search history.

(56) References Cited

U.S. PATENT DOCUMENTS

| | | | | |
|---|---|---|---|---|
| 2006/0178833 | A1* | 8/2006 | Bauer | G01N 15/1475 |
| | | | | 702/19 |
| 2008/0212866 | A1* | 9/2008 | Lett | G01N 21/6428 |
| | | | | 382/133 |
| 2011/0211741 | A1* | 9/2011 | Nakano | G01N 15/1434 |
| | | | | 382/128 |
| 2012/0033064 | A1 | 2/2012 | Tatsuki et al. | |
| 2012/0200694 | A1* | 8/2012 | Garsha | G01N 21/6456 |
| | | | | 348/79 |
| 2014/0310635 | A1* | 10/2014 | Lett | G01N 21/6428 |
| | | | | 715/771 |
| 2014/0350395 | A1* | 11/2014 | Shachaf | A61B 5/444 |
| | | | | 600/431 |
| 2017/0191937 | A1* | 7/2017 | Levenson | G01N 21/6458 |
| 2017/0343475 | A1* | 11/2017 | Yamada | G01N 21/6428 |
| 2018/0052108 | A1* | 2/2018 | Sofue | G01N 21/64 |

FOREIGN PATENT DOCUMENTS

| | | |
|---|---|---|
| JP | 2012-037432 | 2/2012 |
| JP | 2012-37432 | 2/2012 |
| JP | 5835536 | 11/2015 |
| JP | 5835536 | 12/2015 |
| WO | WO2015/146938 | 10/2015 |

OTHER PUBLICATIONS

International Patent Application No. PCT/JP2017/000965; Int'l Preliminary Report on Patentability; dated Jul. 24, 2018; 5 pages.
Supplemental European Search Report issued in corresponding EP Application No. 17741300.2, dated Oct. 23, 2018.
International Search Report issued in parent PCT Application No. PCT/JP2017/000965, dated Apr. 4, 2017.
EP Office Action issued in corresponding EP Application No. 17741300.2, dated Aug. 14, 2019.
Japan Patent Application No. 2017-562541; Notice of Reasons for Refusal; dated Feb. 25, 2020; 6 pages.

* cited by examiner

Luminal A
Luminal B(HER2(-))
Luminal B(HER2(+))
HER2-enriched
Basel-like(TN)

IMAGE PROCESSING APPARATUS AND COMPUTER-READABLE RECORDING MEDIUM STORING PROGRAM

This application claims priority to Japanese Patent Application No. 2016-007778 filed on Jan. 19, 2016 including the description, claims, abstract and drawings, the entire disclosure of which is incorporated herein by reference.

TECHNOLOGICAL FIELD

The present invention relates to an image processing apparatus and a program.

DESCRIPTION OF THE RELATED ART

In pathological diagnosis, it is widely practiced to judge degree of malignancy of a lesion on the basis of expression of a specific biological substances in a tissue specimen.

Specifically, for example, the presence or absence of expression of the specific biological substances for each cell is judged from a microscopic image obtained by photographing a tissue specimen stained by an immunohistochemical method using an enzyme (DAB or the like) or a fluorescent substance, to be used for diagnosis.

In recent years, in order to grasp the degree and kind of the lesion in detail and to perform effective treatment, there is a demand for a technology capable of grasping the expression status of a plurality of kinds of biological substances in a tissue specimen.

For example, breast cancer is classified into five subtypes on the basis of the combination of the presence or absence of expression of hormone receptors (estrogen receptor (ER) and progesterone receptor (PgR)), HER2, and Ki67. Since the properties of cancer cells are different depending on the subtype of the cancer, it is necessary to select suitable medication therapy (e.g., chemotherapy, hormonal therapy, and anti-HER2 therapy) for each subtype.

Conventionally, a pathologist has carried out such a pathological diagnosis by viewing a microscopic image, however, there was a problem that diagnostic results were different for each pathologist and that quantitative determination was difficult.

According to the microscope system described in Patent Document 1, from an image of a tissue specimen in which cell(s) and target molecule(s) are stained, the cell(s) expressing the target molecule(s) are extracted and displayed. In the case of using a tissue specimen in which a plurality of biological substances are stained with dyes having different colors as a target substance, it is possible to grasp expression patterns of the presence or absence of the plurality of kinds of biological substances on cells. Cancers can be classified into some kinds on the basis of the combination of the expression patterns.

PRIOR ART DOCUMENT

Patent Document

[Patent Document 1] Japanese Patent Application Laid Open Publication No. 2011-179924

SUMMARY

Problems to be Solved by the Invention

However, according to the system described in Patent Document 1, it is only possible to grasp the expression patterns of the presence or absence of the target molecules in the specimen, and the expression cannot be quantitatively evaluated.

If the target molecule is stained with a fluorescent dye, expression levels can be evaluated to some extent based on the luminance value of luminescence. However, since the relationship between the luminance value and the expression levels of the biological substances changes depending on the kind of the fluorescent substance, imaging conditions, and the like, it is not possible to evaluate the expression levels of the plurality of kinds of biological substances based on a simple comparison result of luminance values of the plurality of kinds of fluorescent substances.

Therefore, according to the system described in Patent Document 1, although it is possible to grasp the kind of lesion based on the expression of the plurality of kinds of biological substances, it was impossible to grasp the degree of the lesion.

A main object of the present invention is to provide an image processing apparatus and a program capable of quantitating the expression levels of the plurality of kinds of biological substances in a tissue specimen and calculating statistical values obtained by analyzing quantitative results.

The above object of the present invention can be attained by the following means.

Means for Solving the Problem

To achieve at least one of the abovementioned objects, according to an aspect of the present invention, an image processing apparatus embodiment includes:

an input receiver into which a fluorescent image and a morphological image are input, the fluorescent image representing expression of a plurality of kinds of biological substances in a tissue specimen in which a fluorescent bright spot represents expression of the biological substances, and the morphological image representing morphology of a cell in the tissue specimen and including a range common to the fluorescent image;

a region extraction means which extracts an observation target region from the morphological image;

a bright spot extraction means which extracts the fluorescent bright spot from the fluorescent image; and a calculating means which calculates a statistical value from a number of the plurality of kinds of biological substances whose expression is represented by the fluorescent bright spots.

To achieve at least one of the abovementioned objects, according to an aspect of the present invention, an example A program for causing a computer to function comprises:

an input receiver into which a fluorescent image and a morphological image are input, the fluorescent image representing expression of a plurality of kinds of biological substances in a tissue specimen in which a fluorescent bright spot represents expression of the biological substances, and the morphological image representing morphology of a cell in the tissue specimen and including a range common to the fluorescent image;

a region extraction means which extracts an observation target region from the morphological image;

a bright spot extraction means which extracts the fluorescent bright spot from the fluorescent image; and a calculating means which calculates a statistical value from a number of the plurality of kinds of biological substances whose expression is represented by the fluorescent bright spots.

Advantageous Effects of Invention

According to the image processing apparatus and the program of the present invention, it is possible to quantitate the expression levels of the plurality of kinds of biological substances in a tissue specimen and calculate statistical values obtained by analyzing the quantitative results.

BRIEF DESCRIPTION OF THE DRAWINGS

The advantages and features provided by one or more embodiments of the invention will become more fully understood from the detailed description given herein below and the appended drawings which are given by way of illustration only, and thus are not intended as a definition of the limits of the present invention.

DETAILED DESCRIPTION OF EMBODIMENTS

Hereinafter, embodiments for carrying out the present invention will be described with reference to the drawings, but the present invention is not limited thereto.

<Configuration of Pathological Diagnosis Support System 100>

Figure 1:
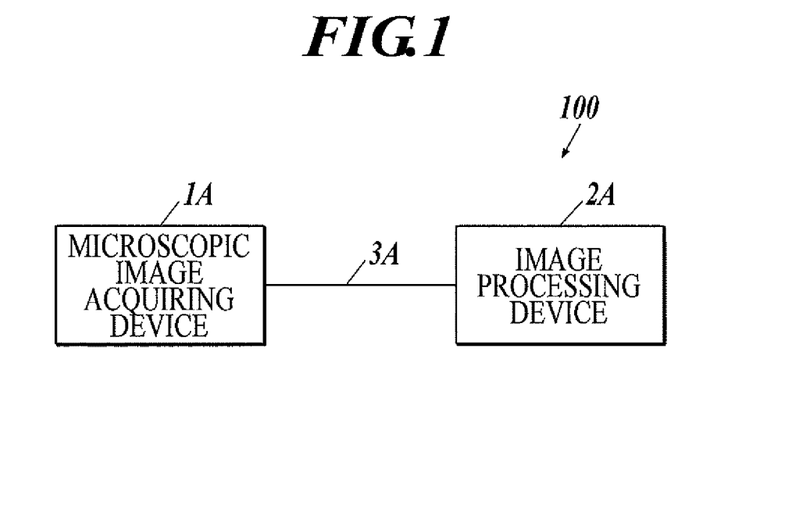
FIG. 1 is a diagram showing a system configuration of a diagnosis support information generation system.

FIG. 1 shows an overall configuration example of a pathological diagnosis support system (diagnosis support information generation system) 100.

The pathological diagnosis support system 100 acquires a microscopic image of a tissue section of a human body stained with predetermined staining reagents and analyzes the acquired microscopic image. The system outputs feature amount which quantitatively represents expressions of specific biological substances in the tissue section of the observation target.

As shown in FIG. 1, the pathological diagnosis support system 100 is configured such that the microscopic image acquiring device (microscope image acquiring apparatus) 1A and the image processing device (image processing apparatus) 2A are connected so as to be able to transmit and receive data via an interface, such as a cable 3A.

The connection between the microscope image acquiring apparatus 1A and the image processing apparatus 2A is not particularly limited. For example, the microscope image acquiring apparatus 1A and the image processing apparatus 2A may be connected via a LAN (Local Area Network) or may be connected wirelessly.

The microscopic image acquiring apparatus 1A is a well-known microscope with a camera which obtains the microscopic image of the tissue section on a slide placed on a slide fixing stage and sends it to the image processing apparatus 2A.

The microscopic image acquiring apparatus 1A includes an irradiating unit, an image forming unit, an imaging unit, a communication I/F, and the like. The irradiating unit includes a light source, a filter, and the like, and irradiates the tissue section on the slide placed on the slide fixing stage with light. The image forming unit includes an ocular lens, an object lens, and the like, and forms an image of transmitted light, reflected light, or fluorescence from the tissue section on the slide due to the irradiated light. The imaging unit is a camera provided in a microscope which includes a CCD (Charge Coupled Device) sensor, and the like, and captures an image on an image forming face formed by the image forming unit to generate digital image data of the microscopic image. The communication I/F transmits the image data of the generated microscopic image to the image processing apparatus 2A.

The microscopic image acquiring apparatus 1A includes a bright field unit combining the irradiating unit and the image forming unit suitable for bright field observation and a fluorescent unit combining the irradiating unit and the image forming unit suitable for fluorescence observation. The bright field/fluorescence observation can be switched by switching the units.

Any known microscope (for example, a phase contrast microscope, a differential interference microscope, an electron microscope, or the like) having a camera may be used as the microscopic image acquiring apparatus 1A.

The microscopic image acquiring apparatus 1A is not limited to a microscope having a camera. For example, a virtual microscope slide creating apparatus which scans a slide on a slide fixing stage of a microscope and obtains a microscopic image of the entire tissue section may be used (for example, see Japanese Patent Application Laid-Open Publication No. 2002-514319). According to the virtual microscope slide creating apparatus, image data can be obtained with which the entire image of the tissue section on the slide can be viewed at once on a display.

The image processing apparatus 2A analyzes the microscopic image transmitted from the microscopic image acquiring apparatus 1A to calculate distributions of specific biological substances in the tissue section of the observation target.

Figure 2:
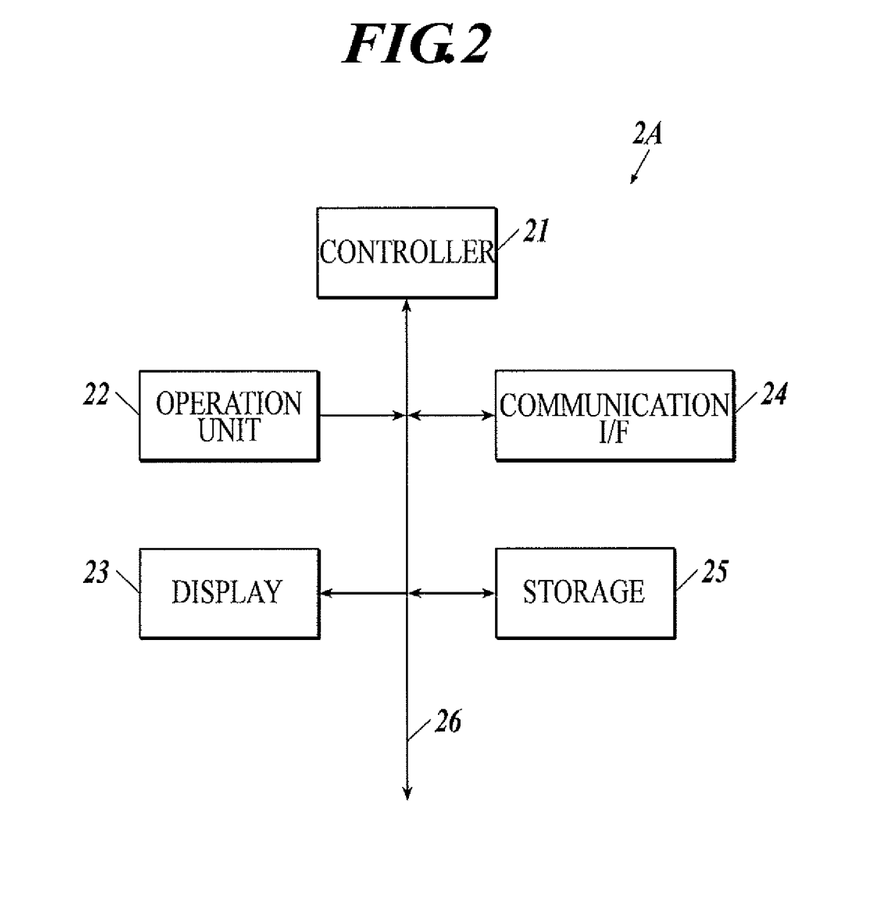
FIG. 2 is a block diagram showing a functional configuration of the image processing device in FIG. 1.

FIG. 2 shows an example of a functional configuration of the image processing apparatus 2A.

As shown in FIG. 2, the image processing apparatus 2A includes a controller 21, an operation means 22, a display 23, a communication I/F 24, a storage 25, and the like, and each unit is connected through a bus 26.

The controller 21 includes a CPU (Central Processing Unit), a RAM (Random Access Memory), and the like, performs various processing in coordination with various programs stored in the storage 25, and collectively controls the operation of the image processing apparatus 2A.

For example, the controller 21 performs image analysis process (see FIG. 3) in coordination with a program stored in the storage 25, and realizes functions as a region extraction means, a fluorescent bright spot extraction means, a calculating means, a classifying means, and a specifying means.

The operation means 22 includes a keyboard provided with character input keys, numeric input keys, and various function keys and a pointing device such as a mouse, and outputs depression signals of the pressed keys of the keyboard and operation signals of the mouse as the input signal to the controller 21.

The display 23 includes, for example, a monitor such as a CRT (Cathode Ray Tube), an LCD (Liquid Crystal Display), and the like, and displays various screens according to an instruction of a display signal input from the controller 21 and realizes functions as a first display and a second display.

The communication I/F 24 is an interface for transmitting and receiving data to and from external devices such as the microscopic image acquiring apparatus 1A. The communication I/F 24 realizes a function as the input receiver of a fluorescent image and a morphological image.

The storage 25 includes, for example, an HDD (Hard Disk Drive), a nonvolatile semiconductor memory, and the like. The storage 25 stores various programs and various pieces of data as described above.

Other than the above, the image processing apparatus 2A may include a LAN adaptor, a router, and the like, and may be connected to external devices through a communication network such as a LAN.

<Images>

In the embodiment, for example, the image processing apparatus 2A preferably analyzes a fluorescent image and a morphological image from the microscopic image acquiring apparatus 1A. Fluorescent bright spots in the fluorescent image represent the expression of a specific biological substance in cells. A predetermined structure in cells is shown in the morphological image (for example, a bright field image showing morphology of cell nucleus of cell membrane).

The bright field image is, for example, a microscopic image acquired by, in the microscopic image acquiring apparatus 1A, forming and capturing an enlarged image of a tissue section stained with a reagent for hematoxylin staining (H-staining reagent) or a reagent for hematoxylin-eosin staining (HE-staining reagent) with a bright field. The bright field image represents morphology of cell(s) in the tissue section. Hematoxylin (H) is a bluish violet dye and stains cell nuclei, bony tissue, a portion of cartilaginous tissue, serous components, and the like (basophilic tissue and the like). Eosin is a red to pink dye and stains cytoplasm, connective tissue of soft tissue, red blood cells, fibrin, endocrine granules and the like (acidophilic tissue and the like).

Examples of the morphological image of cell(s) may include, other than the bright field image, a fluorescent image obtained by capturing fluorescence emitted from a fluorescent staining reagent which is used for staining a tissue section and which can specifically stain a cell structure to be diagnosed. Examples of the fluorescent staining reagent used for obtaining the morphological image include DAPI staining reagent for staining cell nuclei, Papanicolaou staining reagent for staining cytoplasm, and the like. Examples of the morphological image also include a phase difference image, a differential interference image, an electron microscope image, and the like.

A "fluorescent image" representing expression of a specific biological substance in cells with fluorescent bright spots is a microscopic image obtained by forming and capturing an enlarged image of the fluorescence emitted by the fluorescent substance by irradiation of the tissue section stained with a fluorescent staining reagent with excitation light having a predetermined wavelength in the microscopic image acquiring apparatus 1A.

A fluorescent staining reagent is a reagent including, for example, fluorescent nanoparticles which specifically bonds and/or reacts with a specific biological substance, but not limited thereto. A reagent containing any fluorescent substance which specifically binds and/or reacts with a specific biological substance can be used. As will be described in detail later, "fluorescent nanoparticles" are nano-sized particles which emit fluorescence in response to irradiation with excitation light. The particles can emit fluorescence enough for representing each molecule of the target biological substance by a bright spot.

Preferably used fluorescent nanoparticles include quantum dots (semiconductor nanoparticles) or nanoparticles containing fluorescent substance inside. Preferably used fluorescent nanoparticles have an emission wavelength within the sensitivity range of the imaging element 20 of the fluorescence microscope 10, specifically, an emission wavelength of 400 to 700 nm.

<Fluorescent Staining Reagent And Staining Method>

Hereinafter, a fluorescent staining reagent and a staining method of a tissue section using the fluorescent staining reagent are described. The fluorescent staining reagent is used for obtaining the fluorescent image representing the expression of a specific biological substance expressed specifically in cells by fluorescent bright spots.

(1) Fluorescent Substance

Examples of the fluorescent substance used in the fluorescent staining reagent include a fluorescent organic dye and a quantum dot (semiconductor particles). Preferably, the substance exhibits emission of visible to near infrared rays having a wavelength within the range from 400 to 1100 nm when excited by ultraviolet to near infrared rays having a wavelength within the range from 200 to 700 nm.

Examples of the fluorescent organic dye include fluorescein dye molecules, rhodamine dye molecules, Alexa Fluor (manufactured by Invitrogen Corporation) dye molecules, BODIPY (manufactured by Invitrogen Corporation) dye molecules, cascade dye molecules, coumarin dye molecules, eosin dye molecules, NBD dye molecules, pyrene dye molecules, Texas Red dye molecules and cyanine dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, and Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (the above are manufactured by Invitrogen Corporation), methoxycoumalin, eosin, NBD, pyrene, Cy5, Cy5.5 and Cy7. These can be used individually, or used by mixing a plurality of kinds thereof.

Usable examples of the quantum dot include quantum dots respectively containing, as a component, II-VI compounds, III-V compounds, and IV elements (called "II-VI quantum dot", "III-V quantum dot" and "IV quantum dot", respectively). These can be used individually, or used by mixing a plurality of kinds thereof.

Specific examples thereof include but are not limited to CdSe, CdS, CdTe, ZnSe, ZnS, ZnTe, InP, InN, InAs, InGaP, GaP, GaAs, Si and Ge.

A quantum dot having a core of any of the above quantum dots and a shell provided thereon can also be used. Hereinafter, as a notation for the quantum dot having a shell, when the core is CdSe and the shell is ZnS, the quantum dot is noted as CdSe/ZnS.

Usable examples of the quantum dot include but are not limited to CdSe/ZnS, CdS/ZnS, InP/ZnS, InGaP/ZnS, Si/SiO2, Si/ZnS, Ge/GeO2, and Ge/ZnS.

A quantum dot surface-treated with an organic polymer or the like may be used as needed. Examples thereof include CdSe/ZnS having a surface carboxy group (manufactured by Invitrogen Corporation) and CdSe/ZnS having a surface amino group (manufactured by Invitrogen Corporation).

(2) Fluorescent Substance-Containing Nanoparticle

The fluorescent substance-containing nanoparticles described above are nanoparticles in which a fluorescent substance is dispersed. The fluorescent substance and the nanoparticles may or may not be chemically bonded with each other.

The material composing the nanoparticles is not particularly limited, and examples thereof include silica, polystyrene, polyactate acid, melamine, and the like.

The fluorescent substance-containing nanoparticles can be produced by a publically-known method.

For example, fluorescent organic dye-containing silica nanoparticles can be synthesized by referring to the synthesis of FITC-containing silica nanoparticles described in Langmuir, vol. 8, page 2921 (1992). A variety of fluorescent organic dye-containing silica nanoparticles can be synthesized by using any desired fluorescent organic dye instead of FITC.

Quantum dot-containing silica nanoparticles can be synthesized by referring to the synthesis of CdTe-containing silica nanoparticles described in New Journal of Chemistry, vol. 33, page 561 (2009).

Fluorescent organic dye-containing polystyrene nanoparticles can be produced by using a copolymerization method using an organic dye having a polymerizable functional group described in U.S. Pat. No. 4,326,008 (1982) or a method of impregnating a fluorescent organic dye into polystyrene nanoparticles described in U.S. Pat. No. 5,326,692 (1992).

Quantum dot-containing polymer nanoparticles can be produced by using the method of impregnating a quantum dot into polystyrene nanoparticles described in Nature Biotechnology, vol. 19, page 631 (2001).

The average particle diameter of the fluorescent substance-containing nanoparticles is not particularly limited, and preferably, from about 30 to 800 nm. A coefficient of variation (=(stantard deviation/average value)×100%) indicating variation of the particle diameter is not particularly limited, but preferably 20% or less.

The average particle diameter is obtained as follows: capturing the electronic microscope picture using the scanning electron microscope (SEM), measuring the cross sectional area of a sufficient number of particles, and obtaining the diameter of a circle having the area of each measured value as the particle diameter. In the present embodiment, the average particle diameter is to be a calculated average of particle diameters from 1000 particles. The coefficient of variation is also to be a value calculated from particle diameter distribution of 1000 particles.

(3) Bonding of Biological Substance-Recognizing Portion and Fluorescent Nanoparticles The biological substance-recognizing portion of the embodiment is a portion which specifically bonds and/or reacts with a target biological substance. In the explanation of the embodiment, fluorescent nanoparticles and the biological substance-recognizing portion are directly bonded with each other in advance and used as the fluorescent staining reagent which specifically bonds and/or reacts with a target biological substance. A "biological substance-recognizing portion" is a portion which specifically bonds and/or reacts with a specific biological substance.

The specific biological substance is not particularly limited as long as there exists a substance specifically bonding with the specific biological substance. Representative examples of the substance include protein (peptide), nucleic acid (oligonucleotide, polynucleotide), and the like.

Therefore, examples of the biological substance-recognizing portion include an antibody which recognizes the protein as an antigen, another protein which specifically bonds with the protein, nucleic acid including a base sequence which hybridizes with the nucleic acid, and the like.

Specific examples of the biological substance recognition portion include anti-HER2 antibody which specifically bonds with the HER2 which is a protein on the surface of the cell, anti-ER antibody which specifically bonds with the estrogen receptor (ER) in the cell nucleus, anti-actin antibody which specifically bonds with the actin forming the cytoskeleton, and the like.

Among the above, anti-HER2 antibody and anti-ER antibody bonded to the fluorescent nanoparticles (fluorescent staining reagent) are preferable because they can be used for selecting drug administration to treat breast cancer.

The bonding form between the biological substance-recognizing portion and the fluorescent nanoparticles is not particularly limited, and examples include, covalent bond, ionic bond, hydrogen bond, coordinate bond, physical adsorption, chemical adsorption, and the like. Bonding with strong bonding force such as covalent bond is preferable due to the stability of bonding.

There can be an organic molecule connecting the biological substance-recognizing portion and the fluorescent nanoparticles. For example, in order to suppress non-specific absorption with the biological substance, a polyethyleneglycol chain, such as SM (PEG) 12 manufactured by Thermo Scientific, can be used.

When the biological substance-recognizing portion is bonded to the fluorescent substance-containing silica nanoparticles, the same process can be applied either the fluorescent substance is the fluorescent organic dye or the quantum dot.

For example, a silane coupling agent which is a compound widely used for bonding inorganic material and organic material can be used. The silane coupling agent is a compound including an alkoxysilyl group providing a silanol group with hydrolysis in one end of the molecule and a functional group such as carboxy group, amino group, epoxy group, aldehyde group, and the like in the other end, and bonds with the inorganic material through an oxygen atom of the silanol group.

Specific examples include mercaptopropyl triethoxysilane, glycidoxypropyl triethoxysilane, aminopropyl triethoxysilane, silane coupling agent including polyethylene glycol chain (for example, PEG-silane no. SIM6492.7 manufactured by Gelest Inc.), and the like.

When the silane coupling agent can be used, two or more kinds can be used together.

Well-known methods can be used as the reaction method between the fluorescent organic dye-containing silica nanoparticles and the silane coupling agent.

For example, the obtained fluorescent organic dye-containing silica nanoparticles can be dispersed in pure water, the aminopropyl triethoxysilane can be added, and the above reaction can be performed at room temperature for 12 hours. After the reaction ends, by centrifugal separation or filtration, it is possible to obtain fluorescent organic dye-containing silica nanoparticles having a surface modified with the aminopropyl group. Next, the amino group is reacted with the carboxy group in the antibody so that the antibody can bond with the fluorescent organic dye-containing silica nanoparticles through amide bond. If necessary, condensing agent such as EDC (1-Ethyl-3-[3-Dimethylaminopropyl] carbodiimide Hydrochloride: manufactured by Pierce (Registered Trademark)) can also be used.

If necessary, a linker compound including a portion which can directly bond with the fluorescent organic dye-containing silica nanoparticles modified with the organic molecule and a portion which can bond with the molecular target substance can be used. For example, when sulfo-SMCC (Sulfosuccinimidyl 4[N-maleimidomethyl]-cyclohexane-1-carboxylate: manufactured by Pierce) which has a portion which selectively reacts with the amino group and a portion which selectively reacts with the mercapto group is used, the amino group of the fluorescent organic dye-containing silica nanoparticles modified with aminopropyl triethoxysilane and the mercapto group in the antibody are bonded, and with this, the fluorescent organic dye-containing silica nanoparticles bonded with the antibody is made.

When the biological substance-recognizing portion is bonded to the fluorescent substance-containing polystyrene nanoparticles, the same process as the quantum dot can be applied either the fluorescent substance is the fluorescent organic dye or the quantum dot. In other words, by impregnating the fluorescent organic dye and the quantum dot in the polystyrene nanoparticles with the functional group such as the amino group, it is possible to obtain the fluorescent substance-containing polystyrene nanoparticles with the functional group, and then by using the EDC or the sulfo-SMCC, the fluorescent substance-containing polystyrene nanoparticles bonded with the antibody is made.

Examples of biological substance-recognizing portion include the antibody which recognizes the following specific antigen, such as M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, c-KIT, C-MET, collagen type IV, Cox-2, cyclin D1, keratin, cytokeratin (high molecular mass), pankeratin, pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, VIII factor related antigen, fassin, FSH, galectin-3, gastrin, GFAP, glucagon, glycophorin A, granzyme B, hCG, hGH, *Helicobacter pyroli*, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda L chain, LH, lysozyme, macrophage, melan A, MLH-1, MSH-2, myeloperoxidase, myogenin, myoglobin, myosin, neurofilament, NSE, p27 (Kipl), p53, p53, p63, PAX 5, PLAP, pneumocystis calini, podoplanin (D2-40), PGR, prolactin, PSA, prostatic acid phosphatase, Renal Cell Carcinoma, 5100, somatostatin, spectrin, synaptophysin, TAG-72, TdT, thyroglobulin, TSH, TTF-1, TRAcP, tryptase, villin, vimentin, WT1, Zap-70, and the like.

The fluorescent nanoparticles may be directly connected to the biological substance-recognizing portion as described above. Otherwise, as in the indirect method in publically-known immunological staining, the fluorescent nanoparticles may be bonded to the biological substance-recognizing portion indirectly in the staining step. Specifically, for example, the tissue sample is reacted with a biotinylated primary antibody with the specific biological substance as antigen, further reacted with a staining reagent including the fluorescent nanoparticles modified by streptavidin, so that the staining is performed by the specific bonding of streptavidin and biotin to form a complex. Furthermore, the tissue sample may be reacted with a primary antibody with the specific protein as an antigen, further reacted with a secondary biotinylated antibody with the primary antibody as an antigen, reacted with the fluorescent nanoparticles modified by streptavidin for staining.

(4) Staining Method

The method of preparing the tissue section is not particularly limited. A tissue section made by publically-known methods can be used. The staining method described below is not limited to a pathological tissue section, and can be applied to cultured cells.

(4.1) Removing Paraffin

A tissue section is immersed in a container with xylene, and paraffin is removed. The temperature is not particularly limited, and the processing can be performed at room temperature. Preferably, the immersing time is 3 minutes or more and 30 minutes or less. The xylene can be changed during the immersion as necessary.

Next, the tissue section is immersed in a container with ethanol, and the xylene is removed. The temperature is not particularly limited, and the processing can be performed at room temperature. Preferably, the immersing time is 3 minutes or more to 30 minutes or less. The ethanol can be changed during the immersion as necessary.

Next, the tissue section is immersed in a container with water to remove the ethanol. The temperature is not particularly limited, and the processing can be performed at room temperature. Preferably, the immersing time is 3 minutes or more and 30 minutes or less. The water can be changed during the immersion as necessary.

(4.2) Activating Processing

Activating processing of the biological substance in the tissue section is performed according to publically-known methods.

The activating conditions are not specifically set, and examples of liquid for activation that can be used include, 0.01 M citric acid buffered solution (pH 6.0), 1 mM EDTA solution (pH 8.0), 5% urea, 0.1 M tris-hydrochloric acid buffered solution. Examples of the heating device that can be used include autoclave, microwave, pressure pan, water bath, and the like. The temperature is not particularly limited, and the processing can be performed at room temperature. The processing can be performed at a temperature of 50 to 130° C. and the amount of time that the processing is performed can be 5 to 30 minutes.

Next, the tissue section after activating processing is immersed in the container with PBS (Phosphate Buffered Saline), and cleaning is performed. The temperature is not limited, and the processing can be performed at room temperature. Preferably, the immersing time is 3 minutes or more to 30 minutes or less. The PBS can be changed during the immersion as necessary.

(4.3) Staining Using Fluorescent Staining Reagent

The PBS dispersion liquid of the fluorescent staining reagent is placed on the tissue section and reacted with the biological substance in the tissue section.

By changing the biological substance-recognizing portion in the fluorescent staining reagent, staining can be applied to various biological substances. When the fluorescent nanoparticles bonded with a plurality of kinds of biological substance-recognizing portion are used as the fluorescent staining reagent, the fluorescent nanoparticles PBS dispersion liquid of each of the above can be mixed in advance, or the liquid can be sequentially placed on the tissue section separately. The temperature is not particularly limited, and the processing can be performed at room temperature. Preferably, the reacting time is 30 minutes or more to 24 hours or less.

Preferably, a publically-known blocking agent such as BSA included in PBS is dropped before staining with the fluorescent staining reagent.

Next, the tissue section after staining is immersed in the container with PBS, and the unreacted fluorescent nanoparticles are removed. The temperature is not particularly limited, and the processing can be performed at room temperature. Preferably, the immersing time is 3 minutes or more to 30 minutes or less. The PBS can be changed during the immersion as necessary. A cover glass is placed on the tissue section to be sealed. A commercially available sealing agent can be used as necessary.

The HE staining with a HE staining reagent is performed in any step before sealing with the cover glass.

(5) Obtaining Fluorescent Image

The microscopic image acquiring apparatus 1A is used to obtain the microscopic image (fluorescent image) of the stained tissue section. The excitation light source and the optical filter for fluorescence detection are suitably selected corresponding to the absorption maximum wavelength and the fluorescent wavelength of the fluorescent substance used in the fluorescent staining reagent.

<Operation of Diagnosis Support Information Generation System 100 (Including Image Processing Method)>

Hereinafter, specific examples are explained regarding an operation of obtaining the morphological image showing a morphology of cells and a fluorescent image showing expression of the plurality of kinds of biological substances in cells and calculating statistics in the diagnosis support information generation system 100, but the present invention is not limited thereto.

Hereinafter, a case where statistical values for classifying a subtype of breast cancer is calculated based on the expression amount of the plurality of biological substances from an image obtained by photographing a tissue section will be described as an example.

Various subtypes are known for breast cancer cells, and it is preferable to perform appropriate treatment depending on the subtype. As shown in Table 1, in general, breast cancer can be classified into five subtypes according to whether the expressions are positive (+) or negative (−), regarding hormone receptors (ER and PgR), HER2, and Ki67.

TABLE 1

| CLASSIFICATION TABLE OF BREAST CANCER TYPES | ER | PgR | HER2 | Ki67 |
| --- | --- | --- | --- | --- |
| Luminal A | + | + | − | − |
| Luminal B(HER2(−)) | + | − | − | + |
| Luminal B(HER2(+)) | + | +/− | + | |
| HER2 - enriched | − | − | + | |
| Basel - like(TN) | − | − | − | |

First, the operator performs HE staining of a tissue section obtained from breast cancer tissue. Subsequently, fluorescent staining of the plurality of kinds of biological substances (ER, PgR, HER2, and Ki67) is performed using fluorescent nanoparticles.

It is preferable that different kinds of biological substances are respectively stained with fluorescent nanoparticles having different light emission characteristics.

As a morphological image representing the morphology of the cell nucleus, a bright field image is obtained.

Subsequently, a bright field image and a fluorescent image are obtained with the microscopic image acquiring apparatus 1A by the following steps (a1) to (a5).

(a1) The operator mounts the tissue section on a slide, and places the slide on a slide fixing stage of the microscopic image acquiring apparatus 1A.

(a2) The bright field unit is set, the capturing magnification and focus are adjusted, and the observation target region in the tissue section is positioned in the visual field.

(a3) Capturing is performed with the capturing means to generate an image data of a bright field image (a morphological image), and the image data is transmitted to the image processing apparatus 2A.

(a4) The unit is changed to the fluorescent unit.

(a5) Capturing is performed with the capturing means without changing the visual field and the capturing magnification to generate an image data of a fluorescent image, and the image data is transmitted to the image processing apparatus 2A.

The step of above (a5) is repeated according to the kinds of the fluorescent nanoparticles used for staining. Specifically, in this embodiment, step of (a5) is repeated four times to obtain four fluorescent images representing luminescence of fluorescent nanoparticles used for staining ER, PgR, HER2, and Ki67, respectively. The excitation light and the filter used for obtaining each fluorescent image are appropriately selected to be combined depending on the light emission characteristics.

Figure 3:
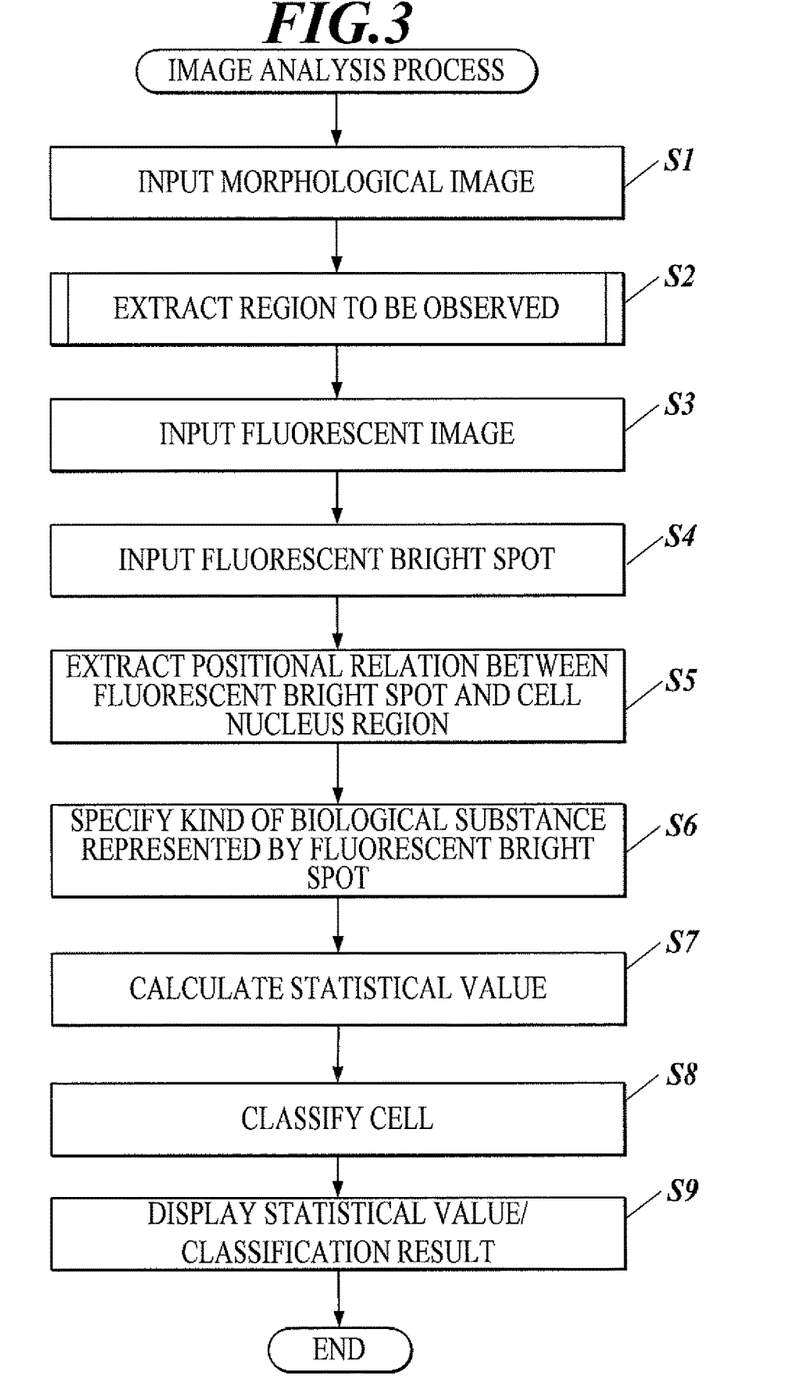
FIG. 3 is a flowchart showing image analysis process of the present invention.

Subsequently, image analysis process is performed in the image processing apparatus 2A to analyze expressions of ER, PgR, HER2, and Ki67 based on the morphological image and the fluorescent image to calculate statistical values. FIG. 3 shows a flowchart of the image analysis process.

The image analysis process according to the present invention is performed by the controller 21 in coordination with the image processing program stored in the storage 25. The controller 21 performs the processing as in the following embodiments in accordance with the image processing program.

First, when the morphological image is input from the microscopic image acquiring apparatus 1A through the communication I/F 24 (step S10: input step), the controller 21 extracts a region of the cell nucleus subjected to HE staining to be stained into bluish violet as an observation target region from the morphological image (step S2: region extraction step).

Figure 4:
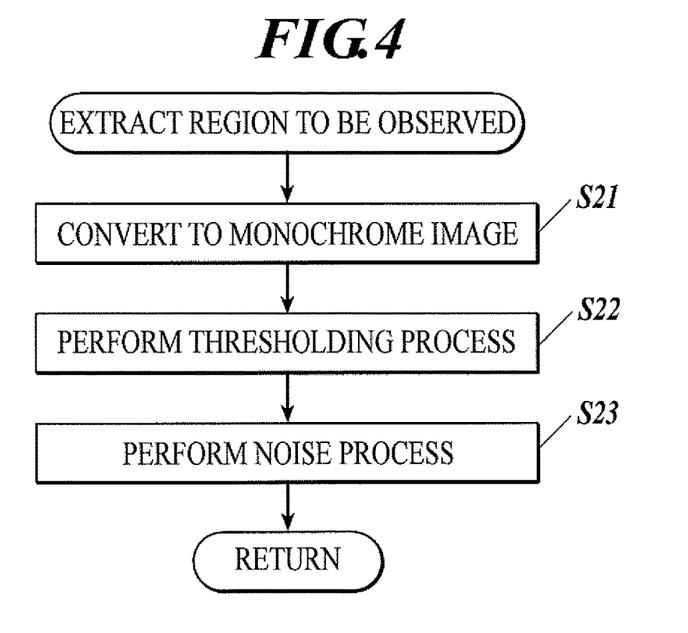
FIG. 4 is a flowchart showing a flow of a region extraction step.

In step S2, as shown in FIG. 4, for example, the morphological image is converted to a monochrome image (step S21), the monochrome image is subjected to threshold processing using a predetermined threshold to binarize each pixel value (step S22), and the binarized image is subjected to noise processing (step S23).

Specifically, the noise processing can be performed by performing closing processing on the binary image. The closing processing is processing of performing dilation processing and then erosion processing by the same number of times. The dilation processing is processing of replacing the target pixel with a white pixel when any of the pixels within the range of n×n pixels (n is an integer of 2 or more) from the target pixel is white. The erosion processing is processing of replacing the target pixel with a black pixel when any of the pixels within the range of n×n pixels from the target pixel is black. Small regions such as noise can be removed by the closing processing.

After the processing of steps S21 to S23 is generated a cell nucleus image including the cell nucleus region extracted from the morphological image.

Next, when the communication I/F 24 inputs fluorescent images obtained by the microscope image acquiring apparatus 1A (step S3: input step), the controller 21 extracts fluorescent bright spots from each fluorescent image (step S4: bright spot extraction step) and extract "coordinate information," "color information," and the like regarding the fluorescent bright spots.

The "coordinate information" of a fluorescent bright spot is, for example, the position of the fluorescent bright spot in a fluorescent image on two-dimensional coordinates. The "color information" a fluorescent spot is, for example, a peak value of the emission wavelength of the fluorescent spot and is extracted on the basis of the fluorescent image from which the fluorescent bright spot is extracted.

The processing in step S4 can be carried out by any known method using, for example, public analysis software ImageJ, software for automatic measurement of total bright spots G-Count manufactured by G-Angstrom Co., Ltd., and the like.

Next, "information on the positional relationship between the fluorescent bright spot and the cell nucleus region" is extracted (step S5). The information on the positional relationship between the fluorescent bright spot and the cell nucleus region is, for example, information on whether or not the fluorescent bright spot is within the cell nucleus region, on the distance to the cell nucleus region nearest to the fluorescent bright spot, and the like. Further, based on the information on the positional relationship, the cell nucleus region belonging to the same cell as the fluorescent bright spot may be discriminated and the discrimination result may be included in the "information on the positional relationship between the fluorescent luminescent spot and the cell nucleus region."

Next, based on the above-described "coordinate information and color information of each fluorescent bright spot", "information on the positional relationship between the cell nucleus region and the fluorescent bright spot", and the like, the "kind of the biological substance represented by the fluorescent bright spot" is specified (Step S6: specifying step).

In step S6, furthermore, processing excluding fluorescent bright spots derived from the background noise may be performed. Specifically, for example, if the distance from the fluorescent bright spot to the nearest cell nucleus region is larger than a predetermined value, the fluorescent bright spot is determined to be extracellular noise and is excluded.

Next, statistical values are calculated from the number of the plurality of kinds of biological substances whose expression is represented by the fluorescent bright spots (step S7: calculating step).

The statistical values relate to, for example, the sum of the expression numbers of each biological substance, the expression number of each biological substance per cell, and the like. Values useful for diagnosis are calculated as appropriate depending on the kind of tissue specimen, lesion, stained biological substance, and the like.

For example, subtype classification of breast cancer is generally performed based on the expression number of ER, PgR, HER2, and Ki67. Therefore, in the present embodiment, first, the expression number of the plurality of kinds of biological substances is calculated for each of the plurality of kinds of biological substance, using the "kind of biological substance represented by the fluorescent bright spot" and information on a cell nucleus region belonging to the same cell as the fluorescent bright spot. Statistical values are calculated regarding the expression levels of the plurality of kinds of biological substances per cell.

Furthermore, it is known that, regarding some kinds of cancer, the closer specific biological substances (hereinafter referred to as a first biological substance and a second biological substance) in the cell is to each other, the higher the malignancy of the cancer is. In diagnosing the malignancy of cancer as described above, for example, first, for each first biological substance is selected a single second biological substance which belongs to the same cell as the first biological substance and which is closest to the first biological substance, and then the distance between the first biological substance and the selected second biological substance is calculated. The expression numbers of the plurality of kinds of biological substances per cell are weighed using the distance averaged for each cell to be used as statistical values.

Next, the cells are classified in accordance with the statistical values (step S8: classification step). An index of classification is preferably prepared in advance and stored in the storage 25, specifically, data (for example, a table) showing a relationship between the classification items such as cancer subtype and degree of malignancy and the expression levels of the plurality of kinds of biological substances. Different indices are prepared according to the kind of tissue specimen, lesion, stained biological substances, and the like.

Table 2 is an example of a table showing the relationship between the subtypes and the malignancy levels of breast cancer and the expression levels of the biological substances. In Table 2, if the expression level per cell is smaller than a threshold value, the expression level of the biological substance is indicated by a score of "−". If the expression level per cell is equal to or higher than the threshold value, the expression level of the biological substance is evaluated to be positive and is indicated by five scores of "+", "++", "+++", "++++", and "+++++" (The more "+"s indicate higher expression level). The hatching in Table 2 regarding Luminal B (HER2 (+)), HER2-enriched, and Basal-like (TN: Triple Negative) indicates that there is no correlation which affects classification between these subtypes and the expression level of Ki67.

TABLE 2

| SUBTYPE | LEVEL | ER | PgR | HER2 | Ki67 |
|---|---|---|---|---|---|
| Luminal A | − | +++ | +++ | − | − |
|  | + | ++++ | ++++ | + | + |
|  | ++ | +++++ | +++++ | ++ | ++ |
| Luminal B(HER2(−)) | − | +++ | − | − | +++ |
|  | + | ++++ | + | + | ++++ |
|  | ++ | +++++ | ++ | ++ | +++++ |
| Luminal B(HER2(+)) | − | +++ | − | +++ |  |
|  | + | ++++ | + | ++++ |  |
|  | ++ | +++++ | ++ | +++++ |  |
| HER2 - enriched | − | − | − | +++ |  |
|  | + | + | + | ++++ |  |
|  | ++ | ++ | ++ | +++++ |  |
| Basel - like(TN) | − | − | − | − |  |
|  | + | + | + | + |  |
|  | ++ | ++ | ++ | ++ |  |

In classifying cells on the basis of TABLE 2, first, in accordance with the statistical value calculated from the expression level of each biological substance per cell in step S7, the expression level of each biological substance for each cell is scored in six levels, from "−" to "+++++". Then, by collating the score of each biological substance with the table and searching the subtype and the level corresponding to the score, classification of subtype and level of the cell is performed.

For example, if the number of biological substance, i.e., HER2, per cell is within the range of 0 to 180 in cells within the image according to statistical values, the range of 0 to 180 are scored into 6 levels. Then, when a score of ER in a certain cell is "+++++", a score of PgR is "++", and a score of HER2 is "+++++", the cell is classified into Luminal B (HER2) on the basis of Table 2.

Figure 5:
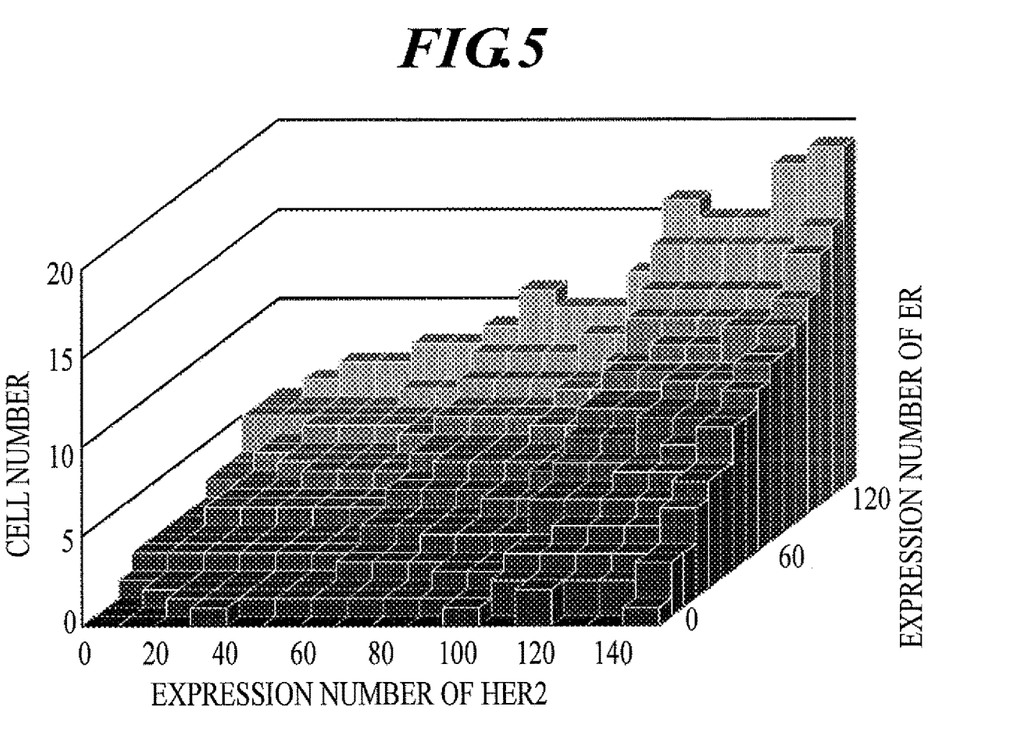
FIG. 5 is an example of a diagram for displaying statistical values.

Next, the calculated statistical values are displayed (step S9: first display step). FIG. 5 is an example of a two-dimensional histogram displaying, as statistical values, the expression numbers of HER2 and ER per cell in the entire screen of the morphological image. The subtype of cells with high HER2 and ER expression is Luminal B (HER2 (+)) according to Table 2. It is easy to grasp that cells whose expression numbers of HER2 and ER per cell are close to the maximum value, that is, cells of Luminal B (HER2 (+)), exist most frequently according to FIG. 5. It should be noted that the items displayed in displaying the statistical values are not limited to the expression numbers of ER and HER2 in FIG. 5, but it is preferable that the operator arbitrarily selects and switches the items.

Figure 6:
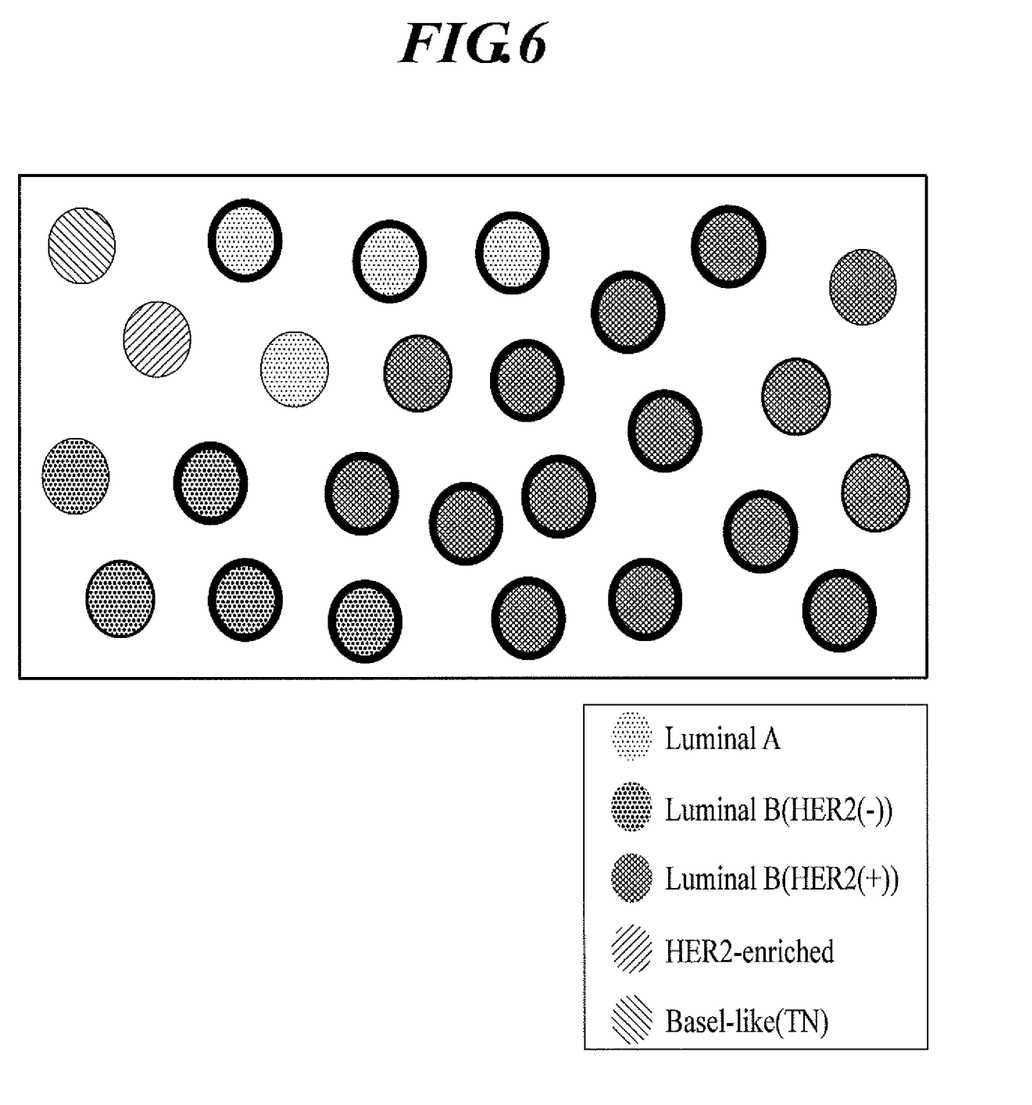
FIG. 6 is a diagram schematically showing a display of cell classification results.

In step S9, the classification result of step S8 may be further displayed (second display step). FIG. 6 is an example of an image displaying cell nucleus regions extracted from the morphological image in a color-coded manner according to the subtype of the cell, which is the classification result, and further, with the thickness of the contour line changed according to the level of malignancy. The image of FIG. 6 and the morphological image may be superimposed and displayed. As a result, it is possible to easily grasp how cells are distributed for each subtype and level of the cancer.

According to the above-described embodiment, it is possible to quantitate the expression levels of the plurality of biological substances in a tissue specimen and to calculate statistical values obtained by analyzing the expression levels of the plurality of biological substances, so that the kind and degree of the lesion can be classified in detail on the basis of the plurality of kinds of biological substances.

As a result, the accuracy of the pathological diagnosis can be improved and a more detailed treatment plan can be established.

The description of the above embodiment is a suitable example of the present invention, and the present invention is not limited thereto.

For example, in the above-described embodiment, the plurality of kinds of biological substances are respectively stained using fluorescent nanoparticles having different light emission characteristics, and fluorescent images are obtained using excitation light and a filter depending on the light emission characteristics, thereby the kinds of the biological substances are determined based on the emission wavelength of the fluorescent nanoparticles. However, depending on the combination of the biological substances to be stained, fluorescent nanoparticles having the same light emission characteristics can be used.

For example, when analyzing expressions of the plurality of kinds of biological substances which is expressed at different positions, such as HER2 expressed on a cell membrane and Ki67 expressed in a cell nucleus, it is possible to discriminate the kinds of the biological substances represented by the fluorescent bright spots based on the positional relationship between the cell nucleus region extracted from the morphological image and fluorescent bright spots extracted from the fluorescent image. Specifically, in step S6, the fluorescent luminescent spot is determined to be Ki67 when it exists in a cell nucleus region, HER2 when it is outside of but within a predetermined distance from a cell nucleus region, and a noise when it is away from the cell nucleus region by the predetermined distance or more.

Further, as the observation target region extracted from the morphological image, in addition to the cell nucleus region, a region of a cell membrane and any structure in cells can be extracted and used. For example, regions of the plurality of kinds of structures, such as a cell nucleus and a cell membrane, may be extracted as observation target regions.

Furthermore, the above description discloses an example which uses an HDD, a semiconductor nonvolatile memory, or the like as the computer readable medium of the program of the present invention, however, the present invention is not limited to the above. A portable recording medium such as a CD-ROM, and the like can be applied as other computer readable media. A carrier wave can be applied as the medium which provides the data of the program of the present invention through a communication line.

Other than the above, the detailed configuration and the detailed operation of each device composing the diagnosis support information generation system 100 can be suitably changed within the scope of the present invention.

INDUSTRIAL APPLICABILITY

As described above, the present invention suitably provides an image processing apparatus and a program which can quantitate the expression levels of the plurality of kinds of biological substances in a tissue specimen and calculate statistical values obtained by analyzing the quantitative results.

DESCRIPTION OF REFERENCE NUMERALS

1A Microscopic image acquiring apparatus
2a Image processing apparatus
21 Controller
22 Operator
23 Display
24 Communication I/F
25 Storage
26 Bus
3a Cable
100 Diagnosis support information generation system

The invention claimed is:
1. An image processing apparatus comprising:
a communication interface into which a fluorescent image and a morphological image are input, the fluorescent image representing expression of a plurality of kinds of biological substances in a tissue specimen in which a fluorescent bright spot represents expression of the biological substances, and the morphological image representing morphology of a cell in the tissue specimen and including a range common to the fluorescent image; and
a controller comprising at least one processor and memory comprising instructions, which when executed by the processor:
extracts an observation target region from the morphological image, extracts the fluorescent bright spot from the fluorescent image, and calculates a statistical value from a number of the plurality of kinds of biological substances whose expression is represented by the fluorescent bright spots, wherein the statistical value is based on a sum of expression numbers for each biological substance.

2. The image processing apparatus according to claim 1, wherein the statistical value is calculated from a number of the plurality of kinds of biological substances per the observation target region.

3. The image processing apparatus according to claim 1, comprising:

a first display which displays the statistical value.

4. The image processing apparatus according to claim 3, wherein the first display displays a graph illustrating the statistical value.

5. The image processing apparatus according to any one of claim 1, wherein the controller classifies the observation target region on a basis of the statistical value.

6. The image processing apparatus according to claim 5, wherein the controller classifies the observation target region on a basis of a table and the statistical value, the table including kinds and expression amounts of the plurality of kinds of biological substances in combination.

7. The image processing apparatus according to claim 5, comprising:

a second display which displays the observation target region identified for each classification.

8. The image processing apparatus according to claim 1, wherein the plurality of kinds of biological substances in the tissue specimen are respectively stained using a plurality of kinds of fluorescent nanoparticles having different emission wavelengths from each other.

9. The image processing apparatus according to claim 8, wherein the controller specifies a kind of biological substance represented by the fluorescent bright spot on a basis of an emission wavelength of the fluorescent bright spot.

10. The image processing apparatus according to claim 1, wherein the controller specifies a kind of biological substance represented by the fluorescent bright spot on a basis of a positional relationship between the observation target region and the fluorescent bright spot.

11. A non-transitory computer-readable recording medium storing a program for causing a computer to function as:

a communication interface in which a fluorescent image and a morphological image are input, the fluorescent image representing expression of a plurality of kinds of biological substances in a tissue specimen in which a fluorescent bright spot represents expression of the biological substances, and the morphological image representing morphology of a cell in the tissue specimen and including a range common to the fluorescent image; and a controller comprising at least one processor which, when instructed by the program, extracts an observation target region from the morphological image, extracts the fluorescent bright spot from the fluorescent image, and calculates a statistical value from a number of the plurality of kinds of biological substances whose expression is represented by the fluorescent bright spots, wherein the statistical value is based on a sum of expression numbers for each biological substance.

12. The image processing apparatus of claim 1, wherein the expression numbers are weighed using a distanced average for each cell.

13. The image processing apparatus of claim 1, wherein the statistical value is calculated based on the expression number of each biological substance per cell.

\* \* \* \* \*